US 6,372,226 B2
(12) United States Patent
Aoki et al.

(10) Patent No.: US 6,372,226 B2
(45) Date of Patent: *Apr. 16, 2002

(54) INTRASPINAL BOTULINUM TOXIN FOR TREATING PAIN

(75) Inventors: Kei Roger Aoki, Coto de Caza; Minglei Cui, Irvine, both of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/797,556

(22) Filed: Mar. 1, 2001

Related U.S. Application Data

(63) Continuation of application No. 09/578,097, filed on May 25, 2000, now Pat. No. 6,235,289, which is a continuation of application No. 09/417,195, filed on Oct. 12, 1999, now Pat. No. 6,113,915.

(51) Int. Cl.[7] ............................................. A61K 39/02

(52) U.S. Cl. ................................. 424/236.1; 424/247.1

(58) Field of Search ........................... 424/236.1, 247.1; 514/2, 262, 261, 14

(56) References Cited

U.S. PATENT DOCUMENTS

| 4,719,231 A | | 1/1988 | Umezawa | |
|---|---|---|---|---|
| 5,714,468 A | * | 2/1998 | Binder | 514/14 |
| 5,721,215 A | * | 2/1998 | Aoki et al. | 514/21 |
| 5,766,605 A | | 6/1998 | Sanders et al. | |
| 5,846,216 A | | 12/1998 | Gonzales et al. | |
| 5,989,545 A | | 11/1999 | Foster et al. | |

FOREIGN PATENT DOCUMENTS

| WO | WO 94/15629 | * | 7/1994 |
|---|---|---|---|
| WO | 96/33273 | | 10/1996 |
| WO | WO98/10754 | | 1/1998 |
| WO | 98/07864 | | 2/1998 |
| WO | 99/17806 | | 4/1999 |

OTHER PUBLICATIONS

Bigalke, H., et al.; Botulinum A Neurotoxin Inhibits Non–Cholinergic Synaptic Transmission in Mouse Spinal Cord Neurons in Culture; *Brain Research*, 360 (1985); 318–324.

Bigalke, H., et al.; Tetanus Toxin and Botulinum A. Toxin Inhibit Release and Uptake of Various Transmitters, as Studied with Particulate Preparations from Rat Brain and Spinal Cord; *Naunyn–Schmeideberg's Arch. Pharmacol* (1981); 316:244–251.

Dixon, W. J.; Efficient Analysis of Experimental Observations; *Ann. Rev. Pharmacol. Toxicol.* (1980); 20:441–462.

Dubuisson, D., et al.; The Formalin Test: A Quantitative Study of the Analgesic Effects of Morphine, Meperidine, and Brain Stem Stimulation in Rats and Cats; *Pain* (1977); 4:161–174.

Duc, C., et al.; Ultrastructural Localization of SNAP–25 Within the Rat Spinal Cord and Peripheral Nervous System; *The Journal of Comparative Neurology* (1995); 365:152–163.

Fauci, A., Harrisson's Principles of Internal Medicine, Fourteenth Edition (1997); McGraw Hill.

Gianino, J., et al.; Intrathecal Drug Therapy for Spasticity and Pain; Springer (1996).

Habermann, E.; Inhibition by Tetanus and Botulinum A Toxin of the Release of ($^3$H)noradrenaline and ($^3$H)GABA from Rat Brain Homogenate; *Experientia* 44 (1988); 224–226.

Habermann, E.; I–Labeled Neurotoxin from Clostridium Botulinum A: Preparation, Binding to Synaptosomes and Ascent to the Spinal Cord; *Naunyn Schmiedeberg's Arch. Pharmacol.*; 281, 47–56 (1974).

Habermann, E., et al.; Tetanus Toxin and Botulinum A and C Neurotoxins Inhibit Noradrenaline Release from Cultured Mouse Brain; *Journal of Neurochemistry*; vol. 51; No. 2 (1988); 522–527.

Hagenah, R., et al.; Effects of Type A Botulinum Toxin on the Cholinergic Transmission at Spinal Renshaw Cells and on the Inhibitory Action at Ia Inhibitory Interneurones; *Naunyn–Schmiedeberg's Arch. Pharmacol.*; 299, 267–272 (1977).

Johnson, E., et al.; Biomedical Aspects of Botulinum Toxin; *J. Toxicol.–Toxin Reviews*; Feb. 18, 1999; 18(1):1–15.

Jung, H. H., et al.; Expression of Neurotransmitter Genes in Rat Spinal Motoneurons After Chemodenervation with Botulinum Toxin; *Neuroscience* (1997); vol. 78, No. 2; 469–479.

Kim, S. H., et al.; An Experimental Model for Peripheral Neuropathy Produced by Segmental Spinal Nerve Ligation in the Rat; *Pain*, 50 (1992); 355–363.

Mochida, S., et al.; Impairment of Syntaxin by Botulinum Neurotoxin $C_1$ or Antibodies Inhibits Acetylcholine Release but not $Ca^{2+}$ Channel Activity; *Neuroscience* (1995); vol. 65; No. 3; 905–915.

Nelson, P.G., et al.; Mouse Spinal Cord in Cell Culture. IV. Modulation of Inhibitory Synaptic Function; *Journal of Neurophysiology*; vol. 40, No. 5; Sep. 1977; 1178–1187.

Osen–Sand, A., et al.; Inhibition of Axonal Growth by SNAP–25 Antisense Oligonucleotides in vitro and in vivo; *Nature*; Jul. 29, 1993; vol. 364; 445–448.

Pearce, L. B., et al.; Pharmacologic Characterization of Botulinum Toxin for Basic Science and Medicine; *Toxicon* (1997); vol. 35, No. 9; 1373–1412.

(List continued on next page.)

Primary Examiner—Jon P. Weber
Assistant Examiner—Patricia Patten
(74) Attorney, Agent, or Firm—Martin A. Voet; Robert J. Baran; Carlos A. Fisher

(57) ABSTRACT

Methods for treating pain by intrathecal administration to a human patient of a therapeutically effective amount of a neurotoxin such as *botulinum* toxin type A are disclosed.

6 Claims, 7 Drawing Sheets

OTHER PUBLICATIONS

Figure 1:
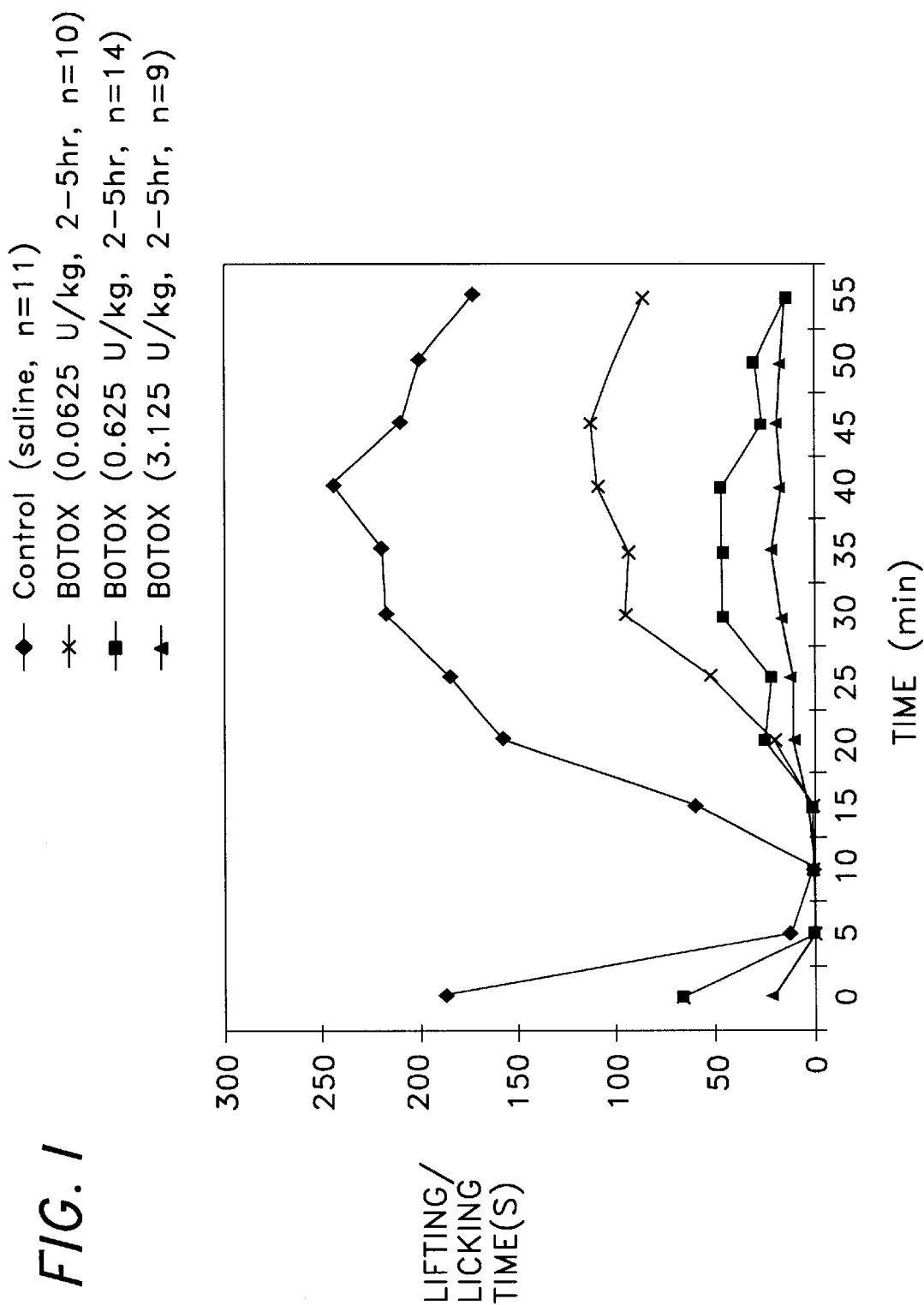

Ransom, B.R., et al.; Mouse Spinal Cord in Cell Culture. I. Morphology and Intrinsic Neuronal Electrophysiologic Properties; *Journal of Neurophysiology*; vol. 40, No. 5; Sep. 1977; 1132–1150.

Ransom, B.R., et al.; Mouse Spinal Cord in Cell Culture. II. Synaptic Activity and Circuit Behavior; *Journal of Neurophysiology*; vol. 40, No. 5; Sep. 1977; 1151–1162.

Ransom, B.R., et al.; Mouse Spinal Cord in Cell Culture. III. Neuronal Chemosensitivity and its Relationship to Synaptic Activity; *Journal of Neurophysiology*; vol. 40, No. 5; Sep. 1977; 1163–1177.

Sanchez–Prieto, J., et al.; Botulinum Toxin A Blocks Glutamate Exocytosis from Guinea–Pig Cerebral Cortical Synaptosomes; *Eur. J. Biochem.* (1987); 165:675–681.

Simpson, L.; Botulinum Toxin: Potent Poison, Potent Medicine; *Hospital Practice*; Apr. 15, 1999; 34(4):87–91.

Tsuda, M., et al.; In vivo Pathway of Thermal Hyperalgesia by Intrathecal Administration of α,β–methylene ATP in Mouse Spinal Cord: Involvement of the Glutamate–NMDA Receptor System; *Br. J. Pharmacol* (1999); 127(2):449–456.

Wiegand, H., et al.; The Action of Botulinum A Neurotoxin on the Inhibition by Antidromic Stimulation of the Lumbar Monosynaptic Reflex; *Naunyn–Schmiedeberg's Arch. Pharmacol.* (1977); 298:235–238.

Williamson, L. C., et al.; Clostridial Neurotoxins and Substrate Proteolysis in Intact Neurons; *The Journal of Biological Chemistry*; Mar. 29, 1996; vol. 271:13; 7694–7699.

Williamson, L. C., et al.; Differential Effects of Tetanus Toxin on Inhibitory and Excitatory Neurotransmitter Release from Mammalian Spinal Cord Cells in Culture; *Journal of Neurochemistry*; 1992; vol. 59:6; 2148–2157.

Woolf, C. J., et al.; Neuropathic Pain: Aetiology, Symptoms, Mechanisms, and Managemnet; *The Lancet*; Jun. 5, 1999; vol. 353; 1959–1964.

Yaksh, T. L., et al.; Chronic Catheterization of the Spinal Subarachnoid Space; *Physiology & Behavior* (1976); vol. 17:1031–1036.

Garzon, et al., "Effect of Intrathecal Injection of Pertussis Toxin on Substance P, Norepinephrine and Serotonin Contents in Various Neural Structures of Arthritic Rats." Life Sciences, vol. 47, pp. 1915–1923 (1990).

Benoliel, et al., "Actions of Intrathecal diphteria toxin–substance P fusion protein on models of persistent pain." vol. 79, No. 2–3 Feb. 1999, pp. 243–253.

Berge, et al., "Selective Neurotoxic Lesions of Descending Serotonerigic and Noradrenergic Pathways in the Rat." Journal of Neurochemistry, vol. 44, No. 4, 1985, pp. 1156–1161.

* cited by examiner

INTRASPINAL BOTULINUM TOXIN FOR TREATING PAIN

CROSS REFERENCE

This application is a continuation of Ser. No. 09/578,097, filed May 25, 2000, now U.S. Pat. No. 6,235,289, which is a continuation of Ser. No. 09/417,195, filed Oct. 12, 1999, now U.S. Pat. No. 6,113,915.

BACKGROUND

The present invention relates to methods for treating pain. In particular, the present invention relates to methods for treating pain by intraspinal administration of a neurotoxin.

Many, if not most ailments of the body cause pain. Generally pain is experienced when the free nerve endings which constitute the pain receptors in the skin as well as in certain internal tissues are subjected to mechanical, thermal or chemical stimuli. The pain receptors transmit signals along afferent neurons into the central nervous system and thence to the brain.

The causes of pain can include inflammation, injury, disease, muscle spasm and the onset of a neuropathic event or syndrome. Ineffectively treated pain can be devastating to the person experiencing it by limiting function, reducing mobility, complicating sleep, and dramatically interfering with the quality of life.

Inflammatory pain can occur when tissue is damaged, as can result from surgery or due to an adverse physical, chemical or thermal event or to infection by a biologic agent. Although inflammatory pain is generally reversible and subsides when the injured tissue has been repaired or the pain inducing stimulus removed, present methods for treating inflammatory pain have many drawbacks and deficiencies. Thus, the typical oral, parenteral or topical administration of an analgesic drug to treat the symptoms of pain or of, for example, an antibiotic to treat inflammatory pain causation factors can result in widespread systemic distribution of the drug and undesirable side effects. Additionally, current therapy for inflammatory pain suffers-from short drug efficacy durations which necessitate frequent drug readministration with possible resulting drug resistance, antibody development and/or drug dependence and addiction, all of which are unsatisfactory. Furthermore, frequent drug administration increases the expense of the regimen to the patient and can require the patient to remember to adhere to a dosing schedule., Neuropathic pain is a persistent or chronic pain syndrome that can result from damage to the nervous system, the peripheral nerves, the dorsal root ganglion or dorsal root, or to the central nervous system. Neuropathic pain syndromes include allodynia, various neuralgias such as post herpetic neuralgia and trigeminal neuralgia, phantom pain, and complex regional pain syndromes, such as reflex sympathetic dystrophy and causalgia. Causalgia is characterized by spontaneous burning pain combined with hyperalgesia and allodynia.

Unfortunately, current methods to treat neuropathic pain, such as by local anesthetic blocks targeted to trigger points, peripheral nerves, plexi, dorsal roots, and to the sympathetic nervous system have only short-lived antinociceptive effects. Additionally, longer lasting analgesic treatment methods, such as blocks by phenol injection or cryotherapy raise a considerable risk of irreversible functional impairment. Furthermore, chronic epidural or intrathecal (collectively "intraspinal") administration of drugs such as clonidine, steroids, opioids or midazolam have significant side effects and questionable efficacy.

Tragically there is no existing method for adequately, predictably and specifically treating established neuropathic pain (Woolf C. et al., *Neuropathic Pain: Aetiology, Symptoms, Mechanisms, and Management*, Lancet 1999;353:1959–64) as present treatment methods for neuropathic pain consists of merely trying to help the patient cope through psychological or occupational therapy, rather than by reducing or eliminating the pain experienced.

Spasticity or muscle spasm can be a serious complication of trauma to the spinal cord or other disorders that create damage within the spinal cord and the muscle spasm is often accompanied by pain. The pain experienced during a muscle spasm can result from the direct effect of the muscle spasm stimulating mechanosensitive pain receptors or from the indirect effect of the spasm compressing blood vessels and causing ischemia. Since the spasm increases the rate of metabolism in the affected muscle tissue, the relative ischemia becomes greater creating thereby conditions for the release of pain inducing substances.

Within the enclosure by the vertebral: canal for the spinal cord by the bones of the vertebrae, the spinal cord is surrounded by three meningeal sheaths which are continuous with those which encapsulate the brain. The outermost of these three meningeal sheaths is the dura matter, a dense, fibrous membrane which anteriorally is separated from the periosteum of the vertebral by the epidural space. Posterior to the dura matter is the subdural space. The subdural space surrounds the second of the three meningeal sheaths which surround the spinal cord, the arachnoid membrane. The arachnoid membrane is separated from the third meningeal sheath, the pia mater, by the subarachnoid or intrathecal space. The subarachnoid space is filled with cerebrospinal fluid (CSF). Underlying the pia mater is the spinal cord. Thus the progression proceeding inwards or in posterior manner from the vertebra is the epidural space, dura mater, subdural space, arachnoid membrane, intrathecal space, pia matter and spinal cord.

Therapeutic administration of certain drugs intraspinally, that is to either the epidural space or to the intrathecal space, is known. Administration of a drug directly to the intrathecal space can be by either spinal tap injection or by catheterization. Intrathecal drug administration can avoid the inactivation of some drugs when taken orally as well and the systemic effects of oral or intravenous administration. Additionally, intrathecal administration permits use of an effective dose which is only a fraction of the effective dose required by oral or parenteral administration. Furthermore, the intrathecal space is generally wide enough to accommodate a small catheter, thereby enabling chronic drug delivery systems. Thus, it is known to treat spasticity by intrathecal administration of baclofen. Additionally, it is known to combine intrathecal administration of baclofen with intramuscular injections of botulinum toxin for the adjunct effect of intramuscular botulinum for reduced muscle spasticity. Furthermore, it is known to treat pain by intraspinal administration of the opioids morphine and fentanyl, as set forth in Gianno, J., et al., *Intrathecal Drug Therapy for Spasticity and Pain*, Springer-Verlag (1996), the contents of which publication are incorporated herein by reference in its entirety.

The current method for intrathecal treatment of chronic pain is by use of an intrathecal pump, such as the SynchroMed® Infusion System, a programmable, implanted pump available from Medtronic, Inc., of Minneapolis, Minn.

A pump is required because the antinociceptive or antispasmodic drugs in current use have a short duration of activity and must therefore be frequently readministered, which readministration is not practically carried out by daily spinal tap injections. The pump is surgically placed under the skin of the patient's abdomen. One end of a catheter is connected to the pump, and the other end of the catheter is threaded into a CSF filled subarachnoid or intrathecal space in the patient's spinal cord. The implanted pump can be programmed for continuous or intermittent infusion of the drug through the intrathecally located catheter. Complications can arise due the required surgical implantation procedure and the known intrathecally administered drugs for pain have the disadvantages of short duration of activity, lipid solubility which permits passage out of the intrathecal space and systemic transport and/or diffusion to higher CNS areas with potential respiratory depression resulting.

Thus, a significant problem with many if not all of the known intrathecally administered drugs used to treat pain, whether administered by spinal tap or by catheterization, is that due to the drug's solubility characteristics, the drug can leave the intrathecal space and additionally due to poor neuronal binding characteristics, the drug can circulate within the CSF to cranial areas of the CNS where brain functions can potentially be affected.

Botulinum Toxin

The anaerobic, gram positive bacterium *Clostridium botulinum* produces a potent polypeptide neurotoxin, *botulinum* toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The *botulinum* toxin can apparently pass unattenuated through the lining of the gut and attack the central nervous system. The highest cranial nerves are affected first, followed by the lower cranial nerves and then the peripheral motor neurons. Symptoms of untreated *botulinum* toxin poisoning can progress from and include medial rectus paresis, ptosis, sluggish pupillary response to light, difficulty walking, swallowing, and speaking, paralysis of the respiratory muscles and death.

*Botulinum* toxin type A is the most lethal natural biological agent known to man. It has been determined that 39 units per kilogram (U/kg) of intramuscular BOTOX®[1] is a $LD_{50}$ in primates. One unit (U) of *botulinum* toxin can be defined as the $LD_{50}$ upon intraperitoneal injection into mice. BOTOX® contains about 4.8 ng of *botulinum* toxin type A complex per 100 unit vial. Thus, for a 70 kg human a $LD_{50}$ of about 40 U/kg would be about 134 ng or 28 vials (2800 units) of intramuscular BOTOX®. Seven immunologically distinct *botulinum* neurotoxins have been characterized, being respectively neurotoxin serotypes A, B, C1, D, E, F and G each of which is distinguished by neutralization with type-specific antibodies. The neurotoxin component is non-covalently bound to nontoxic proteins to form high molecular weight complexes. The different serotypes of botulinum toxin vary in the animal species that they affect and in the severity and duration of the paralysis they evoke. For example, it has been determined that *botulinum* toxin type A is 500 times more potent, as measured by the rate of paralysis produced in the rat, than is *botulinum* toxin type B. Additionally, *botulinum* toxin type B has been determined to be non-toxic in primates at a dose of 480 U/kg which is about 12 times-the primate $LD_{50}$ for botulinum toxin type A (Moyer E et al., *Botulinum Toxin Type B: Experimental and Clinical Experience*, being chapter 6, pages 71–85 of "Therapy With *Botulinum* Toxin", edited by Jankovic, J. et al. (1994), Marcel Dekker, Inc.)

[1]*botulinum* toxin type A purified neurotoxin complex, available from Allergan, Inc., of Irvine, Calif. A *botulinum* toxin type A complex is also available from Porton Products, Ltd., U.K. under the trade name DYSPORT)

Minute quantities of *botulinum* toxin have been used to reduce excess skeletal and smooth muscle and sphincter contraction. The *botulinum* toxin can be injected directly into the hyperactive or hypertonic muscle or its immediate vicinity and is believed to exert its effect by entering peripheral, presynaptic nerve terminals at the neuromuscular junction and blocking the release of acetylcholine. The affected nerve terminals are thereby inhibited from stimulating muscle contraction, resulting in a reduction of muscle tone. Thus, when injected intramuscularly at therapeutic doses, *botulinum* toxin type A can be used to produce a localized chemical denervation and hence a localized weakening or paralysis and relief from excessive involuntary muscle contractions.

Clinical effects of peripheral intramuscular *botulinum* toxin type A are usually seen within one week of injection. The typical duration of symptomatic relief from a single intramuscular injection of *botulinum* toxin type A averages about three months. Muscles therapeutically treated with a *botulinum* toxin eventually recover from the temporary paralysis induced by the toxin, due possibly to the development of new nerve sprouts or to reoccurrence of neurotransmission from the original synapse, or both. A nerve sprout may establish a new neuromuscular junction. Thus, neuromuscular transmission can gradually return to normal over a period of several months.

In skeletal and smooth muscle tissues *botulinum* toxin appears to have no appreciable affinity for organs or tissues other than cholinergic neurons at the neuromuscular junction where the toxin binds to and is internalized by neuronal receptors and, as indicated, block presynaptic release of the neurotransmitter acetylcholine, without causing neuronal cell death.

*Botulinum* toxins have been used for the treatment of an increasing array of disorders, relating to cholinergic nervous system transmission, characterized, for example, by hyperactive neuromuscular activity in specific focal or segmental striated or smooth muscle regions. Thus, intramuscular injection of one or more of the *botulinum* toxin serotypes has been used to treat, blepharospasm, spasmodic torticollis, hemifacial spasm, spasmodic dysphonia, oral mandibular dystonia and limb dystonias, myofacial pain, bruxism, achalasia, trembling chin, spasticity, juvenile cerebral palsy, hyperhydrosis, excess salivation, non-dystonic tremors, brow furrows, focal dystonias, tension headache, migraine headache and lower back pain. Not infrequently, a significant amount of pain relief has also been experienced by such intramuscular therapy. These benefits have been observed after local intramuscular injection of, most commonly *botulinum* toxin type A, or one or another of the other *botulinum* neurotoxin serotypes. *Botulinum* toxin serotypes B, C1, D, E and F apparently have a lower potency and/or a shorter duration of activity as compared to *botulinum* toxin type A at a similar dosage level.

Although all *botulinum* toxins serotypes apparently inhibit release of the neurotransmitter acetylcholine at the neuromuscular junction, they do so by affecting different neurosecretory proteins and/or cleaving these proteins at different sites. For example, *botulinum* types A and E both cleave the 25 kiloDalton (kD) synaptosomal associated protein (SNAP-25), but they target different amino acid sequences within this protein. *Botulinum* toxin types B, D, F and G act on vesicle-associated protein (VAMP, also called synaptobrevin), with each serotype cleaving the protein at a different site. Finally, *botulinum* toxin type C1 has been shown to cleave both syntaxin and SNAP-25. These differences in mechanism of action may affect the relative potency and/or duration of action of the various *botulinum* toxin serotypes.

The molecular weight of a secreted *botulinum* toxin protein molecule, for all seven of the known *botulinum* toxin serotypes, is about 150 kD. Interestingly, the *botulinum* toxins are released by Clostridial bacterium as complexes comprising the 150 kD *botulinum* toxin protein molecule along with associated non-toxin proteins. Thus, the *botulinum* toxin type A complex can be produced by Clostridial bacterium as 900 kD, 500 kD and 300 kD forms. *Botulinum* toxin types B and C1 is apparently produced as only a 500 kD complex. *Botulinum* toxin type D is produced as both 300 kD and 500 kD complexes. Finally, *botulinum* toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the *botulinum* toxin molecule comprise the relevant neurotoxin complex) may act to provide stability against denaturation to the *botulinum* toxin molecule and protection against digestive acids when toxin is ingested. Additionally, it is possible that the larger (greater than about 150 kD molecular weight) *botulinum* toxin complexes may result in a slower rate of diffusion of the *botulinum* toxin away from a site of intramuscular injection of a *botulinum* toxin complex.

The biochemical mechanism of the effects of *botulinum* toxin upon central nervous tissues is controversial. Additionally, the number of CNS neurotransmitters affected as well as the extent and nature of the effect of *botulinum* toxin upon the synthesis, release, accumulation and metabolism of different CNS neurotransmitters is still being determined. In vitro studies have indicated that *botulinum* toxin inhibits potassium cation induced release of both acetylcholine and norepinephrine from primary cell cultures of brain tissue. Additionally, it has been reported that *botulinum* toxin inhibits the evoked release of both glycine and glutamate in primary cultures of spinal cord neurons and that in brain synaptosome preparations *botulinum* toxin inhibits the release of each of the neurotransmitters acetylcholine, dopamine, norepinephrine, CGRP and glutamate.

*Botulinum* toxin type A can be obtained by establishing and growing cultures of *Clostridium botulinum* in a fermenter and then harvesting and purifying the fermented mixture in accordance with known procedures. All the *botulinum* toxin serotypes are initially synthesized as inactive single chain proteins which must be cleaved or nicked by proteases to become neuroactive. The bacterial strains that make *botulinum* toxin serotypes A and G possess endogenous proteases and serotypes A and G can therefore be recovered from bacterial cultures in predominantly their active form. In contrast, *botulinum* toxin serotypes C1, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the *botulinum* toxin type B serotype only cleave a portion of the toxin produced. The exact proportion of nicked to unnicked molecules depends on the length of incubation and the temperature of the culture. Therefore, a certain percentage of any preparation of, for example, the *botulinum* toxin type B toxin is likely to be inactive, possibly accounting for the known significantly lower potency of *botulinum* toxin type B as compared to *botulinum* toxin type A. The presence of inactive *botulinum* toxin molecules in a clinical preparation will contribute to the overall protein load of the preparation, which has been linked to increased antigenicity, without contributing to its clinical efficacy. Additionally, it is known that *botulinum* toxin type B has, upon intramuscular injection, a shorter duration of activity and is also less potent than *botulinum* toxin type A at the same dose level.

What is needed therefore is a method for effectively treating pain and/or spasm by intraspinal administration of a pharmaceutical which has the characteristics of long duration of activity, low rates of diffusion out of an intrathecal space where administered, low rates of diffusion to other intrathecal areas outside of the site of administration, specificity for the treatment of pain and limited or insignificant side effects at therapeutic dose levels.

SUMMARY

The present invention meets this need and provides methods for effectively treating pain by intraspinal administration of a neurotoxin which has the characteristics of long duration of activity, low rates of diffusion out of an, for example, intrathecal space where administered, low rates of diffusion to other intrathecal areas outside of the site of administration, specificity for the treatment of pain and limited or insignificant side effects at therapeutic dose levels.

A method for treating pain according to the present invention can have the step of intraspinal administration of a neurotoxin to a mammal, thereby alleviating pain experienced by the mammal. Preferably, the neurotoxin used is a *botulinum* toxin, such as one of, or a combination of one or more, of the *botulinum* toxin serotypes A, B, C, D, E, F and G. Most preferably, the *botulinum* toxin used is *botulinum* toxin type A because of the high potency, ready availability and long history of clinical use of *botulinum* toxin type A to treat various disorders.

The neurotoxin intraspinally administered according to the methods of the present invention has not been conjugated, attached, adhered to or fused to and is not administered in conjunction with a neuronal targeting moiety. A neuronal targeting moiety is a compound which functionally interacts with a binding site on a neuron causing a physical association between the targeting moiety and/or a conjugate attached to the targeting moiety and the surface of the neuron, such as a primary sensory afferent. Thus, the targeting moiety provides specificity for or binding affinity for one or more type of neurons. In the present invention, any pharmaceutical preparation (i.e. a reconstituted solution of neurotoxin, sodium chloride (saline) and a stabilizer such as albumin) which incorporates a neurotoxin for use according to the disclosed methods is devoid of or essentially free of any deliberately attached or prepared neuronal targeting moiety.

Use of one or more targeting moiety artifacts or constructs is excluded from the scope of the present invention as unnecessary because we have surprisingly discovered that intraspinal neurotoxin administration according to the present invention provides significant pain alleviation even though the neurotoxin is not administrated in conjunction with any non-native or non-inherent to the neurotoxin neuronal targeting moiety. Thus, we unexpectedly discovered that a native neurotoxin, such as *botulinum* toxin type A, can upon intraspinal administration interact with neurons of the CNS and provide alleviation of pain even though the neurotoxin has not been artificially or manipulatively accorded any neuronal specificity or binding affinity, such as by attachment of a neuronal targeting moiety to the neurotoxin. Prior to our invention, it has been believed, as discussed infra, that a neurotoxin, such as *botulinum* toxin type A, would upon intraspinal, including intrathecal, administration, exert widespread, unfocused, diffuse and deleterious effects upon the CNS, such deleterious effects including spasticity. Hence, the assumed necessity for a neuronal targeting moiety deliberately attached to the neurotoxin to attenuate or eliminate these presumed detrimental effects resulting from intraspinal administration of a neurotoxin, such a *botulinum* toxin type A.

We have surprising found that a *botulinum* toxin, such as *botulinum* toxin type A, can be intraspinally administered in amounts between about $10^{-3}$ U/kg and about 60 U/kg to alleviate pain experienced by a mammal, such as a human patient. Preferably, the *botulinum* toxin used is intraspinally administered in an amount of between about $10^{-2}$ U/kg and about 50 U/kg. More preferably, the *botulinum* toxin is administered in an amount of between about $10^{-1}$ U/kg and about 40 U/kg. Most preferably, the *botulinum* toxin is administered in an amount of between about 1 U/kg and about 30 U/kg. In a particularly preferred embodiment of the present disclosed methods, the *botulinum* toxin is administered in an amount of between about 1 U/kg and about 20 U/kg and in some clinical settings the *botulinum* toxin can advantageously be administered in an amount of between about 1 U/kg and about 10 U/kg. Significantly, the pain alleviating effect of the present disclosed methods can persist for up to 10 days or for up to 20 days and depending upon factors, such as the dosage used, for up to 3 months per neurotoxin administration.

The intraspinal administration of the neurotoxin is preferably by intrathecal administration, such as intrathecally to a cranial, cervical, thoracic, lumbar, sacral or coccygeal region of the central nervous system and the administration step can include the steps of accessing a subarachnoid space of the central nervous system of the mammal, and injecting the neurotoxin into the subarachnoid space. The accessing step can be carried out by effecting a spinal tap.

Alternately, the intraspinal administration step can include the steps of catheterization of a subarachnoid space of the central nervous system of the mammal, followed by injection of the neurotoxin through a catheter inserted by the catheterization step into the subarachnoid space. Note that prior to the injecting step there can be the step of attaching to or implanting in the mammal an administration means for administering the neurotoxin to the central nervous system of the mammal. The administration means can be made up of a reservoir of the neurotoxin, where the reservoir is operably connected to a pump means for pumping an aliquot of the neurotoxin out of the reservoir and into an end of the catheter in the subarachnoid space.

It is important to note that the administration step can be carried out prior to the onset of or subsequent to the occurrence of a nociceptive (inflammatory, neuropathic, injury induced, resulting form a cancer, spasm, etc) event or syndrome experienced by the mammal. Thus, the administration step can be carried out between about more than 0.5 hour before to about 14 days before the onset of the nociceptive event. More preferably, administration step is carried out between about more than 0.5 hour before to about 10 days before the onset of the nociceptive event. Most preferably, the administration step is carried out between about more than 0.5 hour before to about 7 days, 4 days, 24 hours or 6 hours before the onset of the nociceptive event. In a particularly preferred embodiment of the present invention, the administration step is carried out between about 2 hours before to about 5 hours before the onset of the nociceptive event. The present methods can be used to treat the pain associated with allodynia.

A detailed embodiment of a method within the scope of the present invention can include the steps of firstly catheterization of a subarachnoid space of the central nervous system of the mammal by making an incision though the dermis of the mammal, and then threading a catheter through the incision into the subarachnoid space, the catheter having an open first end and a remote open second end. Secondly, attaching to or implanting in the mammal an administration means for administering a *botulinum* toxin to the subarachnoid space of the central nervous system of the mammal, the administration means comprising a reservoir for holding a multidose amount of the *botulinum* toxin, the reservoir being connected to a pump means for pumping an aliquot of the *botulinum* toxin out of the reservoir and into the first end of a catheter, the first end of the catheter being connected to the pump means. Thirdly, activating the pump means, and finally, injecting into the subarachnoid space of the central nervous system of the mammal and through the second end of the catheter between about $10^{-3}$ U/kg and about 60 U/kg of the *botulinum* toxin, thereby alleviating pain experienced by the mammal.

Another preferred method within the scope of the present invention is a method for the in vivo attenuation of a nociceptive activity or experience of a human patient, the method comprising the step of intraspinal administration to a human patient a therapeutically effective amount of a *botulinum* toxin, thereby causing an in vivo attenuation of a nociceptive activity or experience of the human patient. The intraspinal administration step can be carried out subsequent to or prior to the occurrence or onset of a nociceptive activity, experience, sensation or syndrome.

A further preferred method within the scope of the present invention is a method for treating pain by selecting a neurotoxin with antinociceptive activity, choosing a portion of a central nervous system of a patient which influences a nociceptive activity; and intraspinally administering to the portion of the central nervous system chosen the neurotoxin selected.

Notably, the neurotoxin used to practice the present methods can be made by a Clostridial bacterium, such as one or more of the *Clostridium botulinum, Clostridium butyricum*, and *Clostridium beratti* species.

Another preferred method within the scope of the present invention is a method for treating pain, the method comprising the step of administering a neurotoxin to the central nervous system or to a dorsal root ganglion of a mammal, thereby alleviating pain experienced by the mammal. A further preferred method within the scope of the present invention is a method for improving patient function, the method comprising the step of administering a neurotoxin to the central nervous system or to dorsal root ganglion of a mammal, thereby improving patient function as determined by improvement in one or more of the factors of reduced pain, reduced time spent in bed, increased ambulation, healthier attitude and a more varied lifestyle.

The present invention also includes within its scope a method which uses a modified neurotoxin. By a modified neurotoxin it is meant a neurotoxin which has had one or more of its amino acids deleted, modified or replaced (as compared to the native neurotoxin) and includes recombinant technology made neurotoxins as well as derivatives and fragments of a recombinant produced neurotoxin.

DRAWINGS

These and other features, aspects, and advantages of the present invention can become better understood from the following description, claims and the accompanying drawings, where in all of FIGS. 1–7 below, "injection" means intrathecal injection.

FIG. 1 is a dose response graph showing that a method within the scope of the present invention alleviates induced inflammatory pain under the rat formalin model. The x axis set forth time in minutes after commencement of the formalin model in rats. The y axis sets forth time spent lifting and licking the formalin injected paw upon use of control (saline, n=11) and BOTOX® (botulinum toxin Type A purified neurotoxin complex) injections at concentrations of 0.0625 U/kg (n=10), 0.625 U/kg (n=14) and 3.125 U/kg (n=9) injected from 2 hours to 5 hours before commencement of the formalin challenge.

Figure 2:
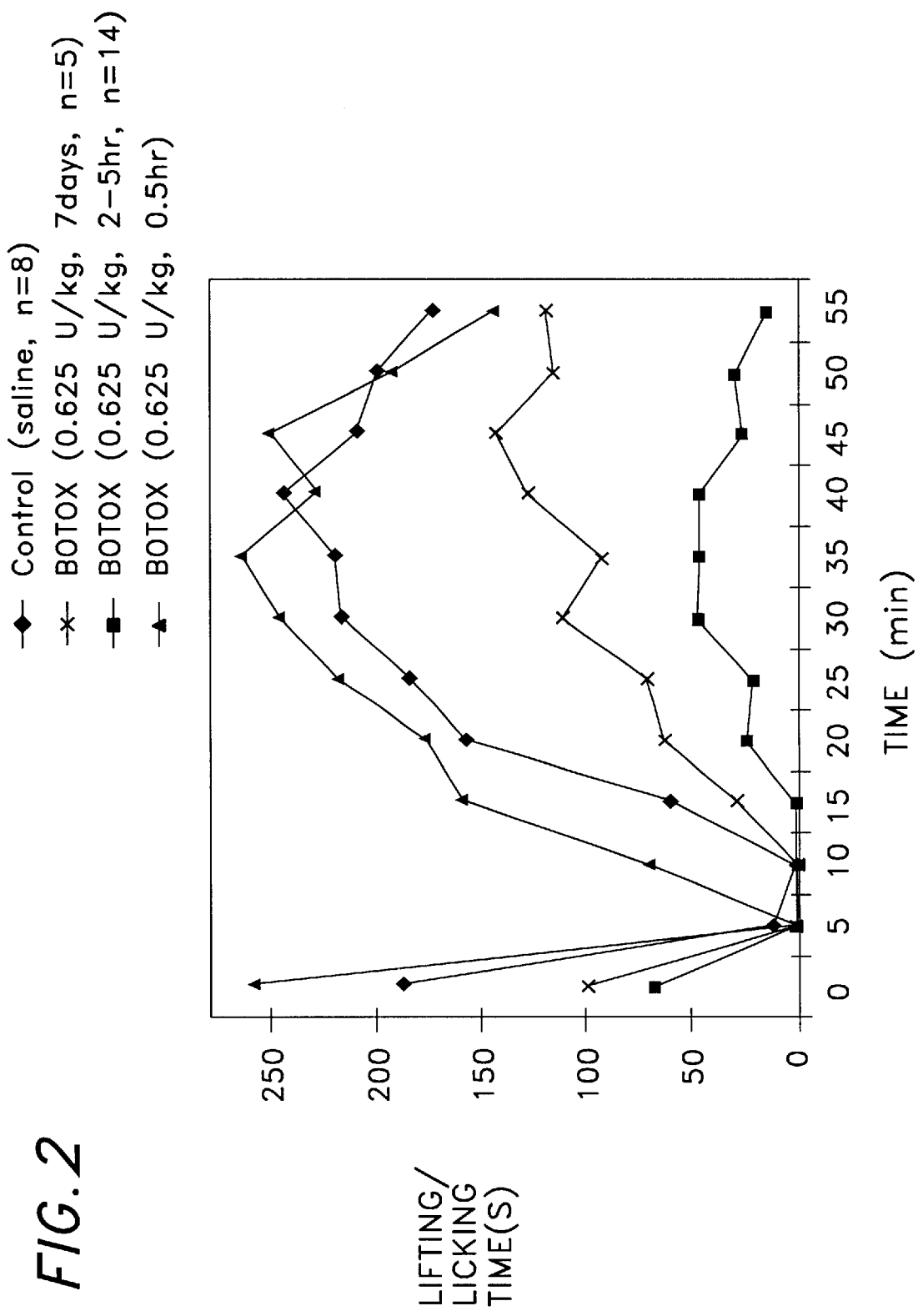

FIG. 2 is a time course graph showing that a method within the scope of the present invention alleviates induced inflammatory pain under the rat formalin model for at least seven days when injected more than one half hour before commencement of the formalin test. The x axis set forth time in minutes after commencement of the formalin model in rats. The y axis sets forth time spent lifting and licking the formalin injected paw upon use of control (saline, n=8) and BOTOX® injections at a concentration of 0.625 U/kg injected 0.5 hour before, 2 hours to 5 hours before (n=14) and 7 days before (n=5) commencement of the formalin challenge.

Figure 3:
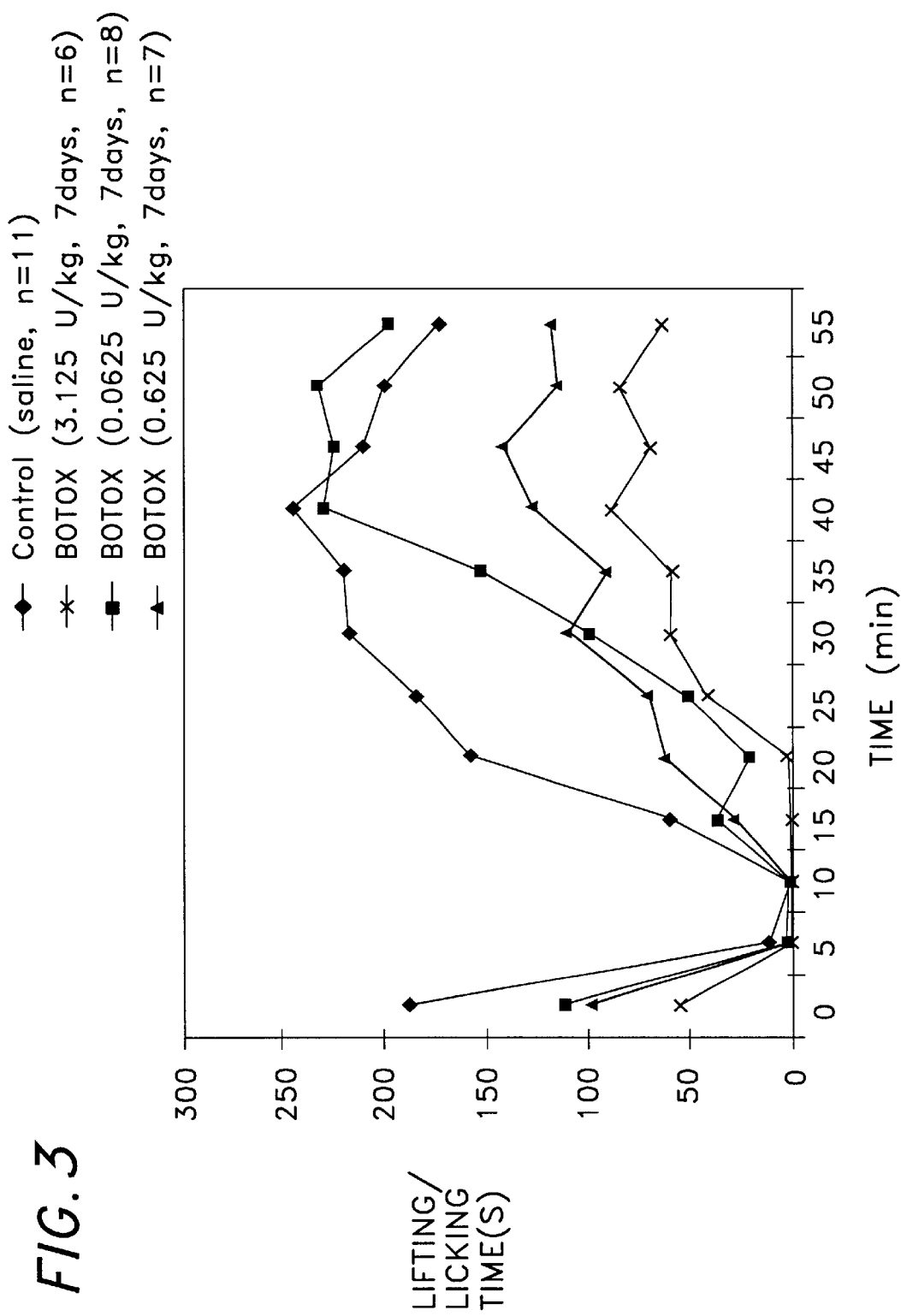

FIG. 3 is a dose response graph showing that a method within the scope of the present invention alleviates induced inflammatory pain under the rat formalin model for at least seven days when different concentrations of botulinum toxin type A are used. The x axis set forth time in minutes after commencement of the formalin model in rats. The y axis sets forth time spent lifting and licking the formalin injected paw upon use of control (saline, n=11) and BOTOX® injections at concentrations of 0.0625 U/kg injected 7 days before (n=8), 0.625 U/kg injected 7 days before (n=7) and 3.125 U/kg injected 7 days before (n=6) commencement of the formalin challenge.

Figure 4:
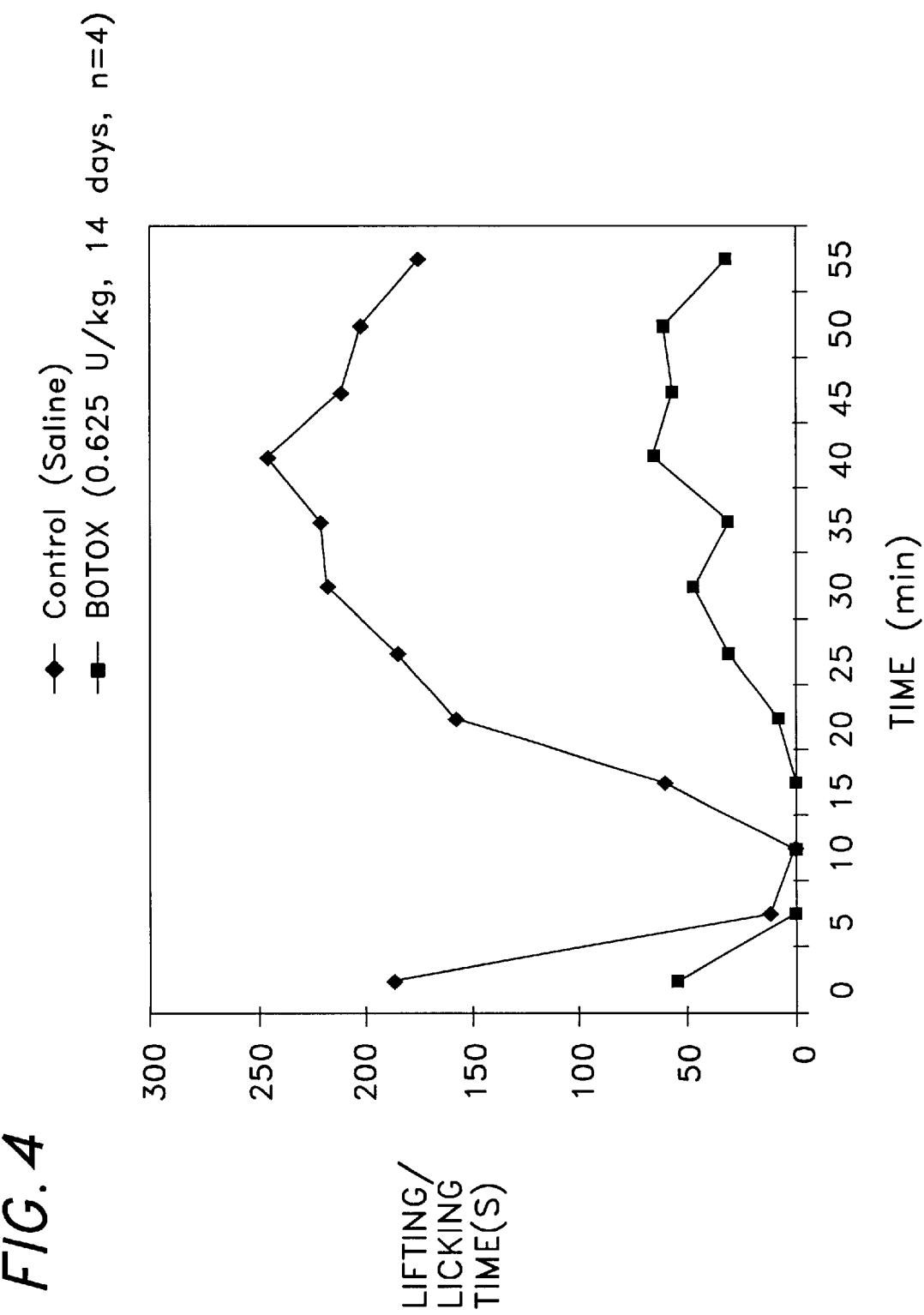

FIG. 4 is a time course graph showing that a method within the scope of the present invention alleviates induced inflammatory pain in the rat formalin model. The x axis set forth time in minutes after commencement of the formalin model in rats. The y axis sets forth time spent lifting and licking the formalin injected paw upon injection of control (saline, n=11), and BOTOX® at a concentration of 0.625 U/kg injected 2 hours 14 days before (n=4) commencement of the formalin challenge.

Figure 5:
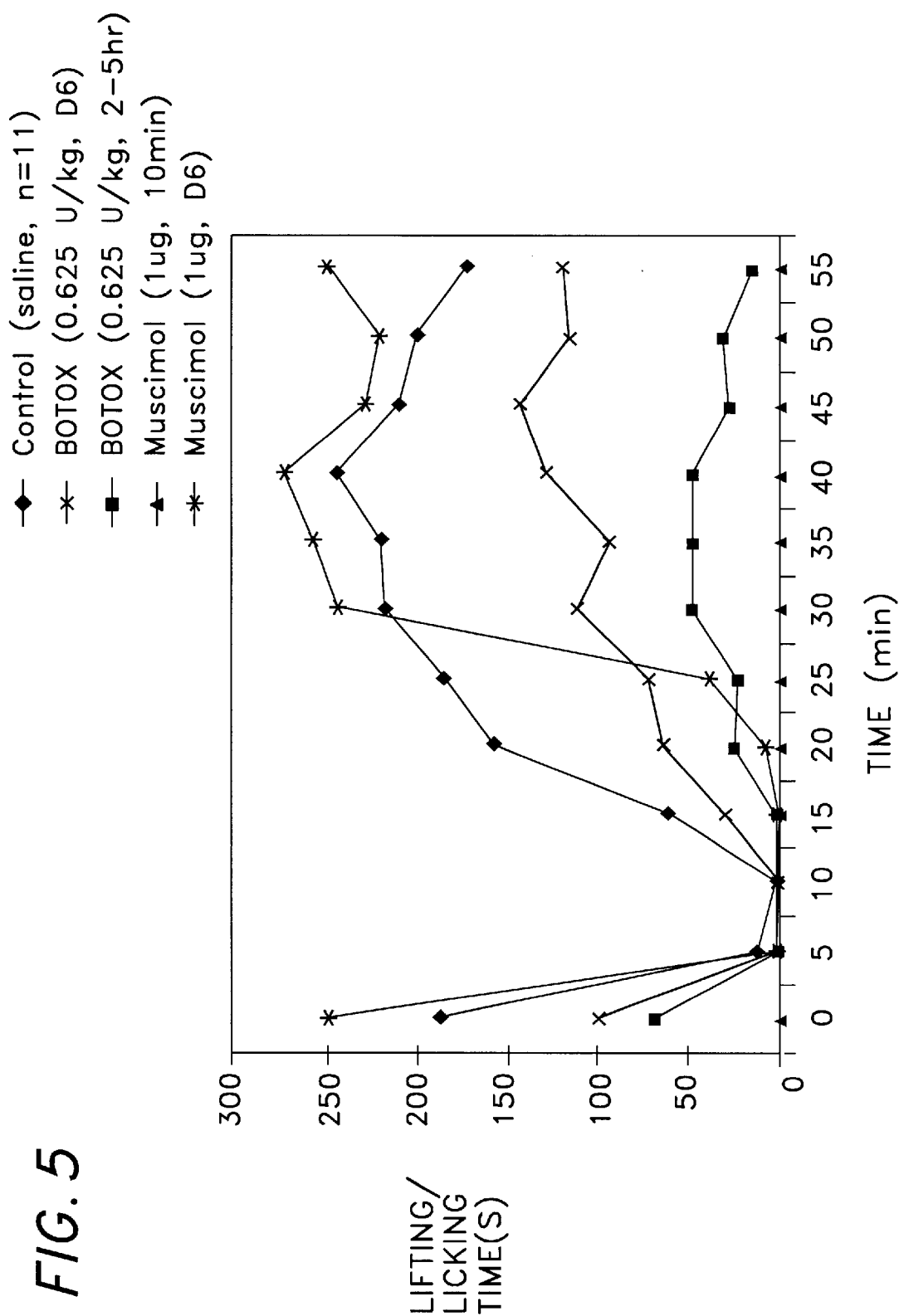

FIG. 5 is a graph which shows a comparison of the analgesic effect of botulinum toxin type A and muscimol upon induced inflammatory pain in the rat formalin model. The x axis set forth time in minutes after commencement of the formalin model in rats. The y axis sets forth time spent lifting and licking the formalin injected paw upon use of control injection (saline, n=11), BOTOX® at a concentration of 0.625 U/kg injected 2 hours to 5 hours before or six days before, and 1 μg of muscimol injected 10 minutes before or six days before commencement of the formalin challenge.

Figure 6:
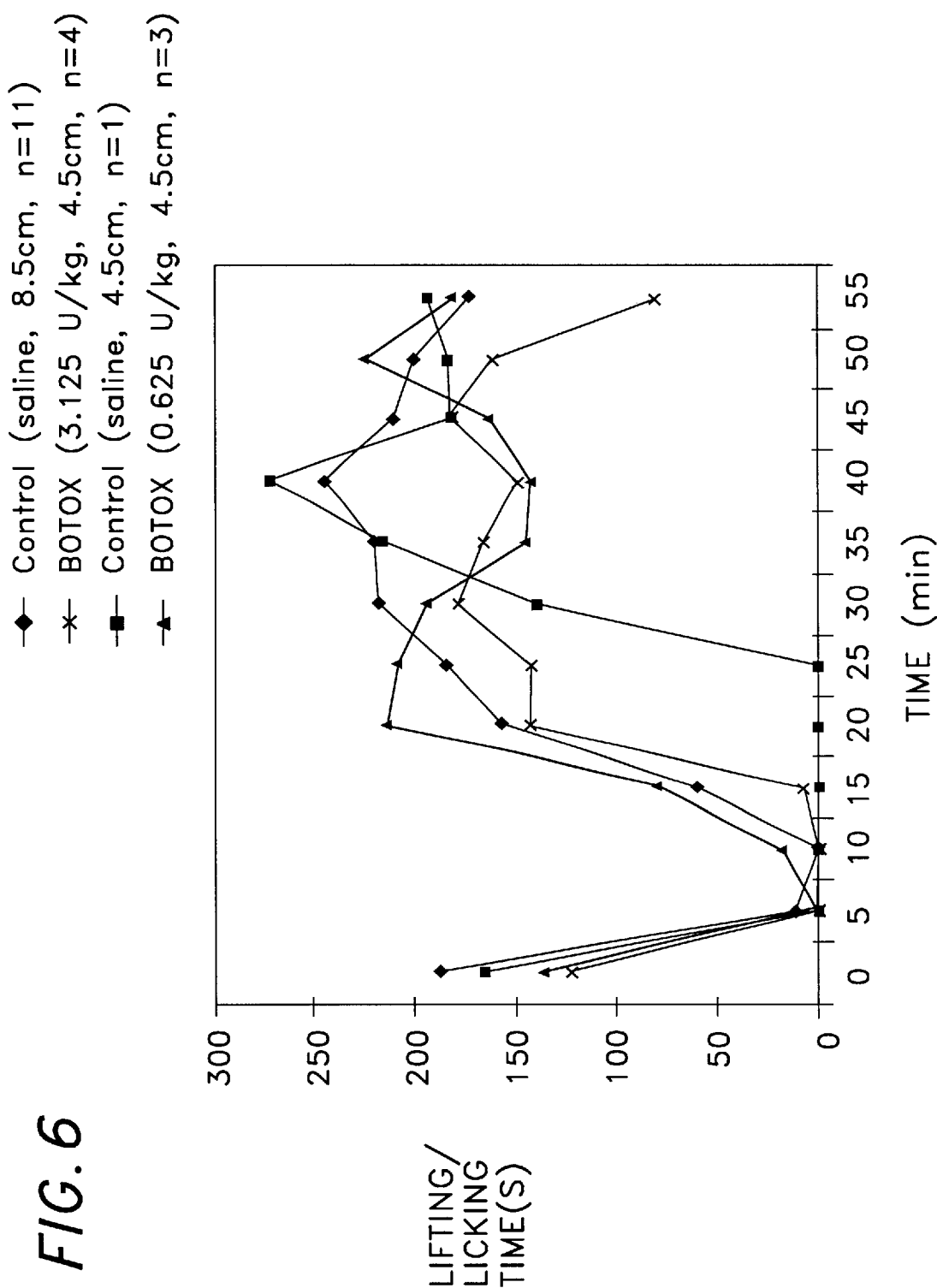

FIG. 6 is graph showing that a method within the scope of the present invention alleviates induced inflammatory pain in the rat formalin model with a local intrathecal analgesic effect. The x axis set forth time in minutes after commencement of the formalin model in rats. The y axis sets forth time spent lifting and licking the formalin injected paw upon use of control where the catheter used for intrathecally injecting saline was located either 4.5 cm (n=1) or 8.5 cm (n=11) caudally (at the lumbar enlargement therefore) from its insertion point, and BOTOX® at a concentration of either 0.625 U/kg (n=3) or 3.125 U/kg (n=4) was injected through a catheter located only 4.5 cm caudally from its insertion point.

Figure 7:
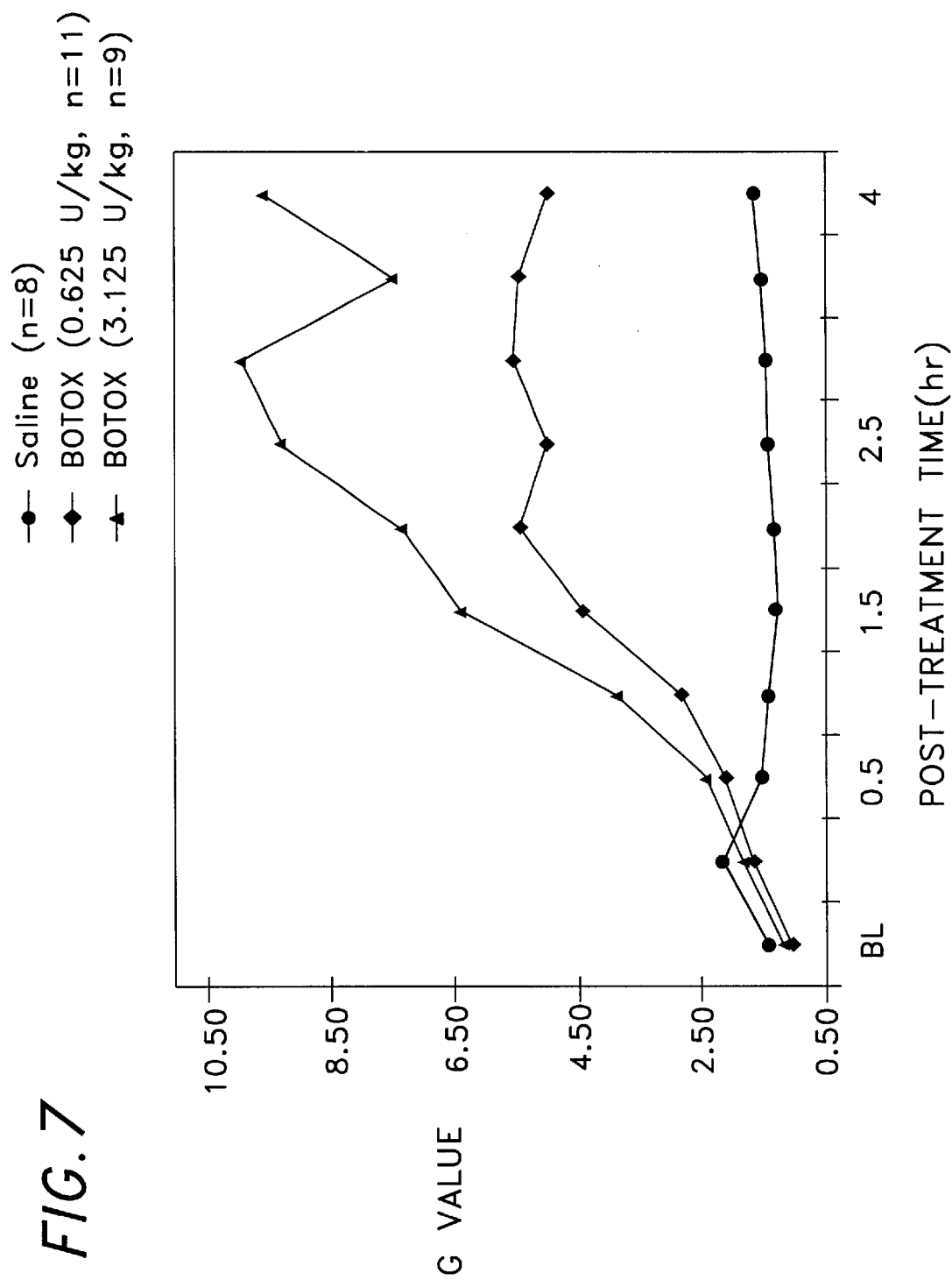

FIG. 7 is a graph showing that a method within the scope of the present invention alleviates surgically induced neuropathic pain. The x axis sets forth time in hours after injection of either saline (n=8) or BOTOX® at a concentration of 0.625 U/kg (n=11) or 3.125 U/kg (n=9). The y axis sets forth the G value, a measure of analgesic effect. BL means baseline.

DESCRIPTION

The present invention encompasses methods for treating pain. We have discovered that intraspinal administration of a neurotoxin to the central nervous system of a patient can result in significant and long lasting alleviation of pain without significant undesirable side effects. Thus, a method within the scope of the present invention provides antinociceptive or analgesic relief.

As used herein "intraspinal" means into or within the epidural space, the intrathecal space, the white or gray matter of the spinal cord or affiliated structures such as the dorsal root and dorsal root ganglia.

Prior to our invention it had been believed by those skilled in the art that intrathecal administration of a neurotoxin, such as a botulinum toxin, would (1) induce significant spasticity in the recipient and (2) promote detrimental effects upon spinal cord and brain functions. Thus, with regard to cited deleterious effect (1): it was reported, as examples, in Williamson et al., in Clostridial Neurotoxins and Substrate Proteolysis in Intact Neurons, J. of Biological Chemistry 271:13;7694–7699 (1996) that both tetanus toxin and botulinum toxin type A inhibit the evoked release of the neurotransmitters glycine and glutamate from fetal mice spinal cord cell cultures, while it was reported by Hagenah et al., in Effects of Type A Botulinum Toxin on the Cholinergic Transmission at Spinal Renshaw Cells and on the Inhibitory Action at Ia Inhibitory Intemeurones, Naunyn-Schmiedeberg's Arch. Pharmacol. 299, 267–272 (1977), that direct intraspinal injection of botulinum toxin type A in experimentally prepared, anaesthetized cats inhibits CNS Renshaw cell activity. Inhibition of central glycine and glutamate neurotransmitter release as well as the downregulation of Renshaw cell activity presumably can both result in vivo in the promotion of significant motorneuron hyperactivity with ensuing peripheral muscle spasticity.

With regard to deleterious effect (2): it is believed that intrathecal administration of the tetanus neurotoxin exerts, by retrograde movement of the tetanus toxin along CNS neurons, significant negative effects upon spinal cord and brain functions, thereby contraindicating intrathecal administration of a related neurotoxin, such as a botulinum toxin. Notably, botulinum toxin and tetanus toxin are both made by Clostridial bacteria, although by different species of Clostridium. Significantly some researchers have reported that botulinum toxin shares, at least to some extent, the noted neural ascent characteristic of tetanus toxin. See e.g. Habermann E.,$^{125}$*I-Labeled Neurotoxin from Clostridium Botulinum A: Preparation, Binding to Synaptosomes and Ascent in the Spinal Cord*, Naunyn-Schmiedeberg's Arch. Pharmacol. 281, 47–56 (1974).

Our invention surprisingly encounters neither of the deleterious effects (1) or (2), and the disclosed methods of the present invention can be practiced to provide effective and long lasting relief from pain and to provide a general improvement in the quality of life experienced by the treated patient. The pain experienced by the patient can be due, for example, to injury, surgery, infection, accident or disease (including cancer and diabetes), including neuropathic diseases and disorders.

Preferably, a neurotoxin used to practice a method within the scope of the present invention is a *botulinum* toxin, such as one of the serotype A, B, C, D, E, F or G *botulinum* toxins. Preferably, the *botulinum* toxin used is *botulinum* toxin type A, because of its high potency in humans, ready availability, and known use for the treatment of skeletal and smooth muscle disorders when locally administered by intramuscular injection. *Botulinum* toxin type B is not a preferred toxin to use in the practice of the disclosed methods because type B is known to have a significantly lower potency and efficacy as compared, to type A, is not readily available, and has a limited history of clinical use in humans.

An intraspinal route for administration of a neurotoxin according to the present disclosed invention can be selected based upon criteria such as the solubility characteristics of the neurotoxin toxin chosen as well as the amount of the neurotoxin to be administered. The amount of the neurotoxin administered can vary widely according to the particular disorder being treated, its severity and other various patient variables including size, weight, age, and responsiveness to therapy. For example, the extent of the area of CNS afferent pain neuron somata influenced is believed to be proportional to the volume of neurotoxin injected, while the quantity of the analgesia is, for most dose ranges, believed to be proportional to the concentration of neurotoxin injected. Furthermore, the particular intraspinal location for neurotoxin administration can depend upon the dermosome location of the pain to be treated. Methods for determining the appropriate route of administration and dosage are generally determined on a case by case basis by the attending physician. Such determinations are routine to one of ordinary skill in the art (see for example, *Harrison's Principles of Internal Medicine* (1997), edited by Anthony Fauci et al., 14$^{th}$ edition, published by McGraw Hill).

Preferably, the intraspinal administration is carried out intrathecally because of the greater ease in which the relatively larger intrathecal space is accessed and because the preferred neurotoxin, a *botulinum* toxin, generally exhibits low solubility in the lipid rich epidural environment. Additionally, epidural neurotoxin administration is a less preferred route of intraspinal administration because the neurotoxin must diffuse through the intrathecal space to have an antinociceptive effect by, it is believed, action upon neurons of the CNS and dorsal root ganglia (DRG). We have found that both inflammatory and neuropathic pain can be effectively treated by the disclosed methods without significant muscle spasticity or flaccidity or other side effects.

Intraspinal administration of a neurotoxin according to the present invention can be by various routes such as by catheterization or by spinal tap injection. The long lasting nature of the therapeutic effects of the present invention substantially removes the need for chronic antinociceptive drug administration, so that the present methods are advantageously practiced by infrequent spinal tap injection of the neurotoxin. Additionally, an intrathecal spinal tap neurotoxin administration route facilitates a more precise and localized delivery of toxin with less danger of damage to the CNS, as compared to moving a catheter to access other CNS locations.

Intrathecal neurotoxin can be administered by bolus injection or by catheterization. The catheter can be inserted at L3-4 or at L4-5, a safe distance from the spinal cord which in humans terminates at L1, and guided upward in the subarachnoid space to rest at the desired site. For pain management, placement of the catheter or location of bolus injection by syringe depends on the site of the perceived pain, and the physicians preference.

It is important to note that therapeutic neurotoxin administration according to the present disclosed methods can be carried out before the occurrence of or during the experience of a nociceptive event or syndrome.

We have found that a neurotoxin, such as a *botulinum* toxin, can be intraspinally administered according to the present disclosed methods in amounts of between about $10^{-3}$ U/kg to about 60 U/kg. A dose of about $10^{-3}$ U/kg can result in an antinociceptive effect if delivered directly to or onto the dorsal horn of the CNS and/or if *botulinum* toxin delivery is assisted by methods such as iontophoresis. Intraspinal administration of less than about $10^{-3}$ U/kg does not result in a significant or lasting therapeutic result. An intraspinal dose of more than 60 U/kg approaches a lethal dose of a neurotoxin such as a *botulinum* toxin. It is desired that the neurotoxin used to obtain either antinociceptive effect contact the nerves of the CNS so as to favorably influence or down regulate the perception of pain or muscle spasm in the innervated organ or tissue. Thus, intraspinal administration of a neurotoxin by, for example, epidural injection can require an increase of the dosage by a factor of about ten to account for dilution of the neurotoxin upon diffusion from the epidural space to the intrathecal space and thence to the exterior nerves of the CNS.

A preferred range for intrathecal administration of a *botulinum* toxin, such as *botulinum* toxin type A, so as to achieve an antinociceptive effect in the patient treated is from about $10^{-2}$ U/kg to about 50 U/kg. Less than about $10^{-2}$ U/kg result in a relatively minor, though still observable, antinociceptive effects, while more than about 50 U/kg can result in some muscle flaccidity and symptoms of toxin intoxication. A more preferred range for intrathecal administration of a *botulinum* toxin, such as *botulinum* toxin type A, so as to achieve an antinociceptive effect in the patient treated is from about $10^{-1}$ U/kg to about 30 U/kg. Less than about $10^{-1}$ U/kg can result in the desired therapeutic effect being of less than the optimal or longest possible duration, while more than about 30 U/kg can still result in some symptoms of muscle flaccidity. A most preferred range for intrathecal administration of a *botulinum* toxin, such as *botulinum* toxin type A, so as to achieve an antinociceptive effect in the patient treated is from about 1 U/kg to about 20 U/kg. Intrathecal administration of a *botulinum* toxin, such as *botulinum* toxin type A, in this preferred range can provide dramatic therapeutic success. Furthermore, our experimental work indicates that a dose range of about 1 U/kg to about 10 U/kg can provide significant and long lasting antinociceptive effect without significant side effects for the treatment of inflammatory and neuropathic pain in human patients.

We have determined by immunohistochemical staining of cleaved SNAP-25 proteins produced by BOTOX®, that intrathecally administered BOTOX® distributes in the superficial layer of the rat dorsal horn, which is the spinal cord layer in which afferent pain fibers terminate. Thus, without wishing to be bound to any particular theory, we hypothesize that the antinociceptive effect of intrathecal *botulinum* toxin is due to its specific inhibition of the release of various neurotransmitters from central terminal afferent sensory neurons and/or from second order projecting neurons in the dorsal horn.

The present invention includes within its scope the use of any neurotoxin which has a long duration antinociceptive effect when locally applied to the central nervous system of a patient. For example, neurotoxins made by any of the species of the toxin producing Clostridium bacteria, such as *Clostridium botulinum, Clostridium butyricum*, and *Clostridium beratti* can be used or adapted for use in the methods of the present invention. Additionally, all of the *botulinum* serotypes A, B, C, D, E, F and G can be advantageously used in the practice of the present invention, although type A is the most preferred and type B the least preferred serotype, as explained above. Practice of the present invention can provide an analgesic effect, per injection, for 3 months or longer in humans.

Significantly, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone.

As set forth above, we have discovered that a surprisingly effective and long lasting treatment of pain can be achieved by intraspinal administration of a neurotoxin to an afflicted patient. In its most preferred embodiment, the present invention is practiced by intrathecal injection of *botulinum* toxin type A. Significantly, we have discovered that dramatic, long term analgesic and/or improved patient function effects can be achieved through intraspinal administration of a neurotoxin by the methods disclosed herein even though the neurotoxin has not had attached or fused to it, by various manipulative techniques or technologies, a neuronal targeting moiety, such as a non-neurotoxin protein, to provide targeting specificity of the neurotoxin for one or more particular types of neurons. Thus, the present invention excludes from its scope the use of any neurotoxins with one or more artificially attached or fused neuronal targeting moieties. A neurotoxin can display a natural binding affinity for a neuron (i.e. for a particular receptor on the surface of the neuron) due to the presence of a binding moiety inherent to the structure of the native neurotoxin molecule (for example, the binding domain of the heavy chain of a *botulinum* toxin, i.e. the $H_c$ fragment). Thus, for clarity "targeting moiety" or "neuronal targeting moiety" as used herein means a targeting moiety which provides to a neurotoxin specific or enhanced neuronal binding affinity and which is not a natural or inherent feature of the neurotoxin which has such a targeting moiety. Contrarily, "binding moiety" as used herein means the inherent component or domain of the native neurotoxin which provides neuronal binding affinity.

The present invention does include within its scope: (a) neurotoxin obtained or processed by bacterial culturing, toxin extraction, concentration, preservation, freeze drying and/or reconstitution and; (b) modified or recombinant neurotoxin, that is neurotoxin that has had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made, but, as stated, excludes neurotoxins with one or more attached neuronal targeting moieties.

*Botulinum* toxins for use according to the present invention can be stored in lyophilized or vacuum dried form in containers under vacuum pressure. Prior to lyophilization the *botulinum* toxin can be combined with pharmaceutically acceptable excipients, stabilizers and/or carriers, such as albumin. The lyophilized material can be reconstituted with saline or water.

EXAMPLES

The following examples provide those of ordinary skill in the art with specific preferred methods within the scope of the present invention for carrying out the present invention and are not intended to limit the scope of what the inventors regard as their invention. Examples 1–4 and 6 show that intrathecal administration of *botulinum* A has an analgesic effect upon inflammatory pain while examples 5 and 7 show that intrathecal administration of *botulinum* A has an analgesic effect upon neuropathic pain.

Example 1

Analgesic Effect of Intrathecally Administered *Botulinum* Toxin Type A Upon Inflammatory Pain The purpose of this experiment was to investigate the analgesic effect of *botulinum* toxin type A on inflammatory pain using the rat formalin model.

Male Sprague-Dawley rats weighing 270 g to 350 g each were anesthetized with isoflurane. In this and in all subsequent Examples intrathecal administration of a neurotoxin was carried out by intrathecal cannulation performed by inserting a PE (polyethylene)-10 tubing about 10 cm long through an incision in the dura over the cisterna and threaded caudally about 8.5 cm down the spinal cord of the rat to the vicinity of the lumbar enlargement, as described in Yaksh T. et al., *Chronic Catheterization of the Spinal Subarachnoid Space*, Physio & Behav 17: 1031–1036 (1976). Either BOTOX® or the control fluid saline was administered intrathecally through the lumbar enlargement located catheter from 0 to 5 hours before the formalin test.

The formalin test to assess analgesia, as set forth in Dubuisson D., et al *The Formalin Test. A Quantitative Study of the Analgesic Effects of Morphine, Merperdine, and Brain Stem Stimulation in Rats and Cats*, Pain, 4 (1977), 161–174, was followed.

Thus, formalin (5%, 50 µl) was injected subcutaneously into rat's right hind paw. We evaluated the number of formalin-evoked flinching responses and the time spent licking the injected paw during time intervals. In the formalin test, recording of the early response (early phase) starts immediately and lasted for 5 min (0–5 min). The recording of the late response (late phase) starts 10 min after formalin injection and lasts for 50 min (10–60 min).

FIG. 1 shows that intrathecal administration of BOTOX® (0.0625 U/kg, 0.625 U/kg or 3.125 U/kg) 2–5 hrs before injection of the formalin reduced the inflammatory pain induced by the formalin model. The control group (n=11) was treated with saline intrathecally. Injection of formalin in rat right hind paw produced a consistent lift/licking and flinch response in the both first 5 min (first phase) and 10–60 min (second phase). BOTOX®) at doses of 0.0625 U/kg (0.003 ng/kg; n=10), 0.625 U/kg (0.03 ng/kg, n=14) and at 3.125 U/kg (0.15 ng/kg, n=9) significantly decreased the lift/licking time during first and second phase. By convention one unit (U) of reconstituted BOTOX® provides a median lethal intraperitoneal dose (LD50) in mice.

The first phase (from time 0 to about plus 5–10 minutes in FIG. 1) is believed to be representative of a short lasting burst of unmyelinated primary afferent neuron activity. In the longer second phase (from about time plus 5–10 minutes in FIG. 1), it is believed that an extended low level of C-fiber activity produces a facilitation in which the output of the WDR (DR meaning dorsal root) neuron is much exaggerated relative to the C-fiber input.

This example shows that intrathecal administration of botulinum toxin type had a significant analgesic effect on inflammatory pain at doses of 0.0625 U/kg (0.003 ng/kg; n=10), 0.625 U/kg (0.03 ng/kg, n=14) and 3.125 U/kg (0.15 ng/kg, n=9) as measured by significantly decreased the lift/licking time during first and second phases.

Example 2

Analgesic Effect of Intrathecally Administered Botulinum Toxin Type A Upon Inflammatory Pain Persists For At Least Fourteen Days Intrathecal cannulation of male Sprague-Dawley rats was carried out as set forth in Example 1. FIG. 2 (control, n=8) shows that pretreatment of rats with BOTOX® (0.03 ng/kg or 0.625 U/kg, n=14) 2 to 5 hrs before injection of formalin reduced the lift/licking time in both the first and second phases. The analgesic effect of BOTOX® persisted for 7 days (0.625 U/kg, n=5) after treatment with BOTOX®, but is diminished compared to the 2 hr pre-treatment (FIG. 2). Additionally, as shown by FIG. 3, the analgesic effect at day 7 after intrathecal botulinum type A administration is dose dependent. Furthermore, as shown by FIG. 4, the analgesic effect of BOTOX® persists for at least 14 days (0.625 u/KG, N=4). As shown by FIG. 2, pretreatment of rats with BOTOX® 0.5 hr before initiation of the formalin challenge failed to reduce the formalin-induced pain.

This example shows that a significant analgesic effect of intrathecal botulinum toxin type A persists for at least 14 days in rats after administration of the toxin. It can be reasonably postulated, extrapolating from the data obtained, that the analgesia persists for at least about 20 days in rats. It can therefore be expected that an anti-inflammatory pain analgesia from intrathecal administration of botulinum toxin type A in humans would persist for at least about 60 days.

Example 3

Comparison of Analgesic Effects of Intrathecally Administered Botulinum Toxin Type A and Muscimol Upon Inflammatory Pain.

Intrathecal cannulation of subject rats was carried out as set forth in Example 1. Either BOTOX® (0.625 U/kg, 2–5 hours before or six days before the formalin test) or the short acting analgesic muscimol (1 µg, 10 minutes before or six days before the formalin test) was administered intrathecally and the formalin test carried out at the indicated subsequent times.

As shown by FIG. 5 (control saline, n=11), the analgesic effect of BOTOX® administered six days prior to the formalin test has a longer duration of analgesic activity, through most of phase 2, as compared to the analgesic effect of intrathecal muscimol administered six days prior to the formalin test. Additionally, FIG. 5 shows that intrathecal BOTOX® administered 2–5 hours before the formalin challenge and intrathecal muscimol ten minutes prior to the formalin challenge resulted in comparable analgesia.

Example 4

Site Specific Analgesic Effect of Intrathecally Administered Botulinum Type A Upon Inflammatory Pain Intrathecal canalization was carried out as set forth in Example 1 with the exception that the catheter was inserted caudally only about 4.5 cm, as opposed to the usual 8.5–10 cm. Control (saline) catheters were inserted at either 8.5 cm (n=11) or at 4.5 cm (n=1) locations. BOTOX® was administered through a catheter inserted caudally 4.5 cm in dosages of either 0.625 U/kg (n=3) or 3.125 U/kg (n=4). The rat formalin test was then carried out. As shown by FIG. 6, there was little or no analgesic effect in the rat formalin test by intrathecal BOTOX® administration through catheters placed at 4.5 cm.

It is known that the heel and bottom of the foot in humans is a dermatome of the fifth lumbar nerve which emanates from the lumbar enlargement (see e.g. plate 150 in Netter, F. Atlas of Human Anatomy, second edition (1997), Novartis), and presumably nerve distribution is similar in the rat. Thus, it can be hypothesized that since the rat plantar, where the formalin is injected, is innervated by nerves which radiate from the lumbar enlargement disposed about 7.5 cm to 9 cm (depending upon the size of the subject rat) caudally down the rat's spinal cord, placement of the intrathecal catheter caudally only 4.5 cm will not result in an analgesic effect if the intrathecally administered BOTOX® exhibits a site specific effect upon spinal cord neurons. And this hypothesis is confirmed by the data shown in FIG. 5.

This example supports both the efficacy and safety of intrathecal botulinum toxin administration to treat pain since we observed that not only did neither a motor deficit or blood pressure alteration occur, at the dosages used, from intrathecal BOTOX® administration, we also determined (FIG. 5) that intrathecal BOTOX® apparently has a localized effect upon the CNS at only the site of it's intrathecal administration.

Example 5

Analgesic Effect of Intrathecally Administered Botulinum Toxin Type A Upon Neuropathic Pain This example investigated whether botulinum toxin type A could reduce the allodynia induced by L5, L6 nerve ligation. Male Sprague Dawley rats (100–120 g) were anesthetized with isoflurane following a surgical neuropathy procedure according to the method set forth in Kim S. et al., An Experimental Model for Peripheral Neuropathy Produced by Segmental Spinal Nerve Ligation in the Rat, Pain, 50 (1992), 355–363. The L6 transverse process was exposed and removed. The L4 and L5 spinal nerves were then isolated and visible and the ligation of L5 was performed by tying tightly with a 3-0 silk thread. The L6 spinal nerve was located just caudal and medial to the sacroiliac junction and was ligated with 6-0 suture. Intrathecal cannulation (as set forth in Example 1) was carried out a month later upon the rats which exhibited allodynia.

Deformities of the hind paw and growth of the toenails were noticed after surgery. Rats developed allodynia by showing sensitive response to normally innocuous mechanical stimuli using the following protocol. Tactile allodynia was measured using von Frey hair aesthesiometers. The rats were tested before (Baseline) and after administration of the *botulinum* toxin type A as BOTOX®. Testing was performed during only the day portion of the circadian cycle. Rats were placed in a plastic cage with a wire mesh bottom which allowed full access to the paws. Environmental acclimation was allowed for approximately 30 minutes until cage exploration and major grooming activities ceased. The area tested was the mid plantar left hind paw in the sciatic nerve distribution, avoiding the less sensitive tori (foot pads). The paw was touched with one of a series of 8 von Frey hairs with experimentally incremental stiffness (0.41, 0.70, 1.20, 2.00, 3.63, 5.50, 8.50, and 15.10 g) (Stoelting). The von Frey hair was presented perpendicular to the plantar surface with sufficient force to cause slight buckling against the paw and held for approximately 6–8 seconds. Stimuli were presented at intervals of several seconds allowing for apparent resolution of any behavioral responses to previous stimuli. A positive response was noted if the paw was sharply withdrawn. Ambulating was considered an ambiguous response, and in such cases the stimulus was repeated. Based on observations on normal, unoperated on rats and healed, sham-operated rats, the cutoff of a 15.10 g hair (approximately 10% of the body weight of the smaller rats) was selected as the upper limit for testing, since stiffer hairs tended to raise the entire limb rather than to buckle, thus substantially changing the nature of the stimulus.

The 50% withdraw threshold (G Value) was determined using the up-down method (Dixon W., *Efficient Analysis of Experimental Observations*, Ann Rev Pharmacol Toxicol 1980, 20: 441–62). In this paradigm testing is initiated with the 2.0 g hair, the middle hair of the series. Stimuli are always presented in a consecutive fashion, whether ascending or descending. In the absence of a paw withdrawal response to the initially selected hair a stronger stimulus is presented. If the paw is withdrawn then the next weaker stimulus is chosen. Optimal threshold calculation by this method requires six responses in the immediate vicinity of the 50% threshold. Since the threshold is not known strings of similar responses may be generated as the threshold is approached from either direction. Accordingly, although all responses are noted, counting of the critical six data points does not begin until the response threshold has been crossed, at which time the two responses straddling the threshold are retrospectively designated as the first two responses of the series of six. Four additional responses to the continued presentation of stimuli that are varied sequentially up or down based on the rat's response constitute the remainder of the series.

Thus, the number of actual responses collected varied from a minimum of 4 (in the case of paw withdrawal sequentially to the first hair, 2.0 g, descending to the weakest hair, 0.4 g: threshold lies below the range of actual stimuli), to a maximum of 9 (in the case of the first withdrawal occurring on the fifth ascending stimulis presentation at 15.1 g followed by elicitation of four additional responses, assuming that the withdrawals continue to occur at or below 15.1 g). In cases where continuous positive or negative responses are observed to continue to occur to the exhaustion of the stimulis set, values of 15.00 g and 0.25 g are assigned respectively. The resulting pattern of positive and negative responses is tabulated using the convention, X=withdrawal (positive response), 0=no withdrawal (negative response), and the 50% response threshold is interpolated using the formula, 50% gram threshold=(10 [$X_f = k\partial$])/10,000, where $X_f$=the value (in log units) of the final von Frey hair use; k=the value from the table prepared for the pattern of positive and negative responses, and; $\partial$=the mean difference (in log units) between stimuli.

FIG. 7 (control, n=8) shows that intrathecal administration of BOTOX® to the neuropathic rats at a concentration of 0.625 U/kg, 0.03 ng/kg (n=11), or at 3.125 U/kg, 0.15 ng/kg (n=9) clearly reduced the allodynia in rats, and that the analgesic effect lasted more than a week. The time intervals along the x axis in FIG. 4 are time after intrathecal administration of the BOTOX®. A higher G value indicates that more force is required before the paw is withdrawn.

The examples above show that intrathecal administration of *botulinum* toxin type A has a pronounced and long lasting analgesic effect upon both inflammatory and neuropathic pain and that the analgesic effect is dose dependent and site specific.

Additional observations showed that at the doses used intrathecal BOTOX® did not produce any significant change in blood pressure and additionally did not cause any significant motor deficit in the subject rats.

Example 6

Treatment of Inflammatory Pain

A patient, age 45, experiencing acute inflammatory pain is treated by intrathecal administration, for example by spinal tap to the lumbar region, with between about 0.1 U/kg and 30 U/kg of *botulinum* toxin type A, the particular toxin dose and site of injection, as well as the frequency of toxin administrations depend upon a variety of factors within the skill of the treating physician, as previously set forth. Within 1–7 days after. toxin administration the patient's pain is substantially alleviated.

The *botulinum* toxin can be injected at different spinal levels to treat different dermosomes, that is to treat pain in various body parts. Additionally, a catheter can be percutaneously inserted into the intrathecal space via lumbar puncture at vertebral level L3-4 or L4-5 using a Tuohy needle. When CSF flow is discernible a silastic catheter is threaded cephalad using a C-arm for verification of catheter placement. The catheter can be advanced to different vertebral locations and/or used at different dose concentrations to treat different types of pain and/or spasm. Thus, the catheter can be placed within the intrathecal space at the dermatomal level of the pain or spasm experienced.

Example 7

Treatment of Neuropathic Pain

A patient, age 36, experiencing pain of neuropathic origin is treated by intrathecal administration through spinal tap to the lumbar region of between about 0.1 U/kg and 30 U/kg of *botulinum* toxin type A. Within 1–7 days the pain symptoms are substantially alleviated.

Example 8

Treatment of Pain Subsequent to Spinal Cord Injury

A patient, age 39, experiencing pain subsequent to spinal cord injury is treated by intrathecal administration, for example by spinal tap or by catheterization, to the spinal cord, such as to the lumbar region of the spinal cord, with between about 0.1 U/kg and 30 U/kg of *botulinum* toxin type A, the particular toxin dose and site of injection, as well as the frequency of toxin administrations depend upon a variety of factors within the skill of the treating physician, as previously set forth. Within 1–7 days after toxin administration the patient's pain is substantially alleviated.

Example 9

Treatment of Pain Subsequent to Limb Injury

A patient, age 51, experiencing pain subsequent to injury to his hand, arm, foot or leg is treated by intrathecal administration, for example by spinal tap or by catheterization, to the spinal cord, such as to the lumbar region of the spinal cord, with between about 0.1 U/kg and 30 U/kg of *botulinum* toxin type A, the particular toxin dose and site of injection, as well as the frequency of toxin administrations depend upon a variety of factors within the skill of the treating physician, as previously set forth. Within 1–7 days after toxin administration the patient's pain is substantially alleviated.

Example 10

Treatment of Pain Associated With Cancer

A patient, age 63, suffering from pain associated with cancer is treated by intrathecal administration, for example by spinal tap or by catheterization, to the spinal cord, such as to the lumbar region of the spinal cord, with between about 0.1 U/kg and 30 U/kg of *botulinum* toxin type A, the particular toxin dose and site of injection, as well as the frequency of toxin administrations depend upon a variety of factors within the skill of the treating physician, as previously set forth. Within 1–7 days after toxin administration the patient's pain is substantially alleviated.

Example 11

Treatment of Pain Associated With Diabetes

A patient, age 47, suffering from pain associated with diabetes is treated by intrathecal administration, for example by spinal tap or by catheterization, to the spinal cord, such as to the lumbar region of the spinal cord, with between about 0.1 U/kg and 30 U/kg of *botulinum* toxin type A, the particular toxin dose and site of injection, as well as the frequency of toxin administrations depend upon a variety of factors within the skill of the treating physician, as previously set forth. Within 1–7 days after toxin administration the patient's pain is substantially alleviated.

An intraspinal neurotoxin administration method for treating pain according to the invention disclosed herein for has many benefits and advantages, including the following:

1. the symptoms of pain can be dramatically reduced.
2. the symptoms of pain can be reduced for from about two to about four months per injection of neurotoxin.
3. the injected neurotoxin tends to exerts a CNS site specific antinociceptive effect.
4. the injected neurotoxin shows little or no tendency to diffuse or to be transported away from the CNS injection site.
5. few or no significant undesirable side effects occur from intraspinal injection of the neurotoxin.
6. the amount of neurotoxin injected intraspinally can be considerably less than the amount of the same neurotoxin required by other routes of administration (i.e. intramuscular, intrasphincter, oral or parenteral) to achieve a comparable effect.
7. The antinociceptive effects of the present methods often result in the desirable side effects of greater patient mobility, a more positive attitude, and an improved quality of life.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes intraspinal administration methods wherein two or more neurotoxins, such as two or more *botulinum* toxins, are administered concurrently or consecutively. For example, *botulinum* toxin type A can be administered intraspinally until a loss of clinical response or neutralizing antibodies develop, followed by administration of *botulinum* toxin type E. Alternately, a combination of any two or more of the *botulinum* serotypes A–G can be intraspinally administered to control the onset and duration of the desired therapeutic result. Furthermore, non-neurotoxin compounds can be intraspinally administered prior to, concurrently with or subsequent to administration of the neurotoxin to proved adjunct effect such as enhanced or a more rapid onset of analgesia before the neurotoxin, such as a *botulinum* toxin, begins to exert its analgesic effect.

Our invention also includes within its scope the use of a neurotoxin, such as a *botulinum* toxin, in the preparation of a medicament for the treatment of pain, by intraspinal administration of the neurotoxin.

Accordingly, the spirit and scope of the following claims should not be limited to the descriptions of the preferred embodiments set forth above.

We claim:

1. A method for alleviating pain, the method comprising the step of intrathecal administration of an effective amount of a *botulinum* toxin to a human patient, thereby alleviating pain experienced by the patient, wherein the *botulinum* toxin has not been modified to exhibit a non-native specificity for a neuron, and wherein the intrathecal administration of the *botulinum* toxin does not cause significant spasticity in the patient.

2. The method of claim 1, wherein the *botulinum* toxin is selected from the group consisting of *botulinum* toxin types A, B, C, D, E, F and G.

3. The method of claim 1, wherein the *botulinum* toxin is *botulinum* toxin type A.

4. The method of claim 1, wherein the *botulinum* toxin is administered in an amount of between about $10^{-3}$ U/kg and about 60 U/kg.

5. A method for alleviating pain, the method comprising the step of intraspinal administration of an effective amount of a *botulinum* toxin type A to a human patient, thereby alleviating pain experienced by the patient, wherein the *botulinum* toxin has not been modified to exhibit a non-native specificity for a neuron, and wherein the intraspinal administration of the *botulinum* toxin type A does not cause significant spasticity in the patient.

6. The method of claim 5, wherein the *botulinum* toxin is administered in an amount of between about $10^{-3}$ U/kg and about 60 U/kg.

* * * * *